United States Patent [19]
Dull et al.

[11] Patent Number: 5,089,701
[45] Date of Patent: Feb. 18, 1992

[54] NONDESTRUCTIVE MEASUREMENT OF SOLUBLE SOLIDS IN FRUITS HAVING A RIND OR SKIN

[75] Inventors: Gerald G. Dull; Richard G. Leffler, both of Athens, Ga.; Gerald S. Birth, Minneapolis, Minn.

[73] Assignee: The United States of America as represented by the Secretary of Agriculture, Washington, D.C.

[21] Appl. No.: 563,170

[22] Filed: Aug. 6, 1990

[51] Int. Cl.$^5$ .............................................. G01N 21/35
[52] U.S. Cl. .................................... 250/341; 250/339; 250/358.1
[58] Field of Search ...................... 250/358.1, 341, 339

[56] References Cited

FOREIGN PATENT DOCUMENTS 1-216265  8/1989  Japan .................................... 250/339

OTHER PUBLICATIONS

Dull et al., "Use of Near Infrared Analysis for the Nondestructive Measurement of Dry Matter in Potatoes" American Potatoe Journal, vol. 66, 1989, pp. 215-225.
Birth et al., "Nondestructive Spectrophotometric Determination of Dry Matter in Onions", Journal American Society of Hort. Sci. 110(2):297-303, 1985.
Dull et al., "Near Infrared Analysis of Soluble Solids in Intact Cantaloupe", Journal Food Sci. 54(2):393-395, Mar./Apr. 1989.

*Primary Examiner*—Carolyn E. Fields
*Attorney, Agent, or Firm*—David R. Sadowski; M. Howard Silverstein

[57] ABSTRACT

The instant invention is drawn to efficient and nondestructive measurement of soluble solids in fruits having a rind or skin, utilizing: infrared radiation source means for providing a beam of near infrared radiation of sufficient intensity to penetrate the fruit, intensity measurement means for measuring the intensity of radiation exiting the fruit, correlating means for correlating the measurements of intensities of the exiting radiation: wherein the near infrared radiation source means and the intensity measurement means are positioned such that when a fruit is positioned within the device, the distance measured along the rind or skin of the fruit between (1) where the center of the beam intersects the rind/skin, and (2) a point on the rind/skin where the center of the field of detection intersects the rind/skin is at least about 8 cm.

23 Claims, 4 Drawing Sheets

NONDESTRUCTIVE MEASUREMENT OF SOLUBLE SOLIDS IN FRUITS HAVING A RIND OR SKIN

FIELD OF THE INVENTION

The present invention relates to use of near infrared (NIR) radiation for nondestructive measurement of soluble solids in fruits having a rind or skin.

BACKGROUND AND SUMMARY OF THE INVENTION

The use of NIR analysis for the nondestructive determination of dry matter in a variety of materials has been described in the literature, see e.g. Dull et al, *Use of Near Infrared Analysis for the Nondestructive Measurement of Dry Matter in Potatoes,* American Potato Journal, Volume 66 (1989) and *Nondestructive Spectrophotometric Determination of Dry Matter in Onions,* Birth et al, Journal American Society of Horticultural Science, 1985, 110(2):297-303. Finally, reference is made to *Near Infrared Analysis of Soluble Solids in Intact Cantaloupe,* Dull et al, published in the Journal of Food Science, 1989, 54(2):393-395.

As can be seen from these references, accurate and rapid determination of soluble solids nondestructively, in a variety of fruits has escaped those who practice in this art. The present invention is of particular benefit in that there is no current reliable nondestructive means to determine fruit quality, especially as it relates to soluble solids, including sugars.

While a fruit can certainly be cut and its contents examined for sugar content, this would destroy the fruit. Further, the purpose of this invention is to nondestructively determine soluble solids (e.g. as a measurement of sugar content) in a quick and efficient manner such that it can be used to grade fruit.

These and other advantages are achieved by the present invention described in greater detail hereinbelow.

BRIEF DESCRIPTIONS OF THE DRAWINGS

DESCRIPTION OF THE PREFERRED EMBODIMENTS

Figure 1:
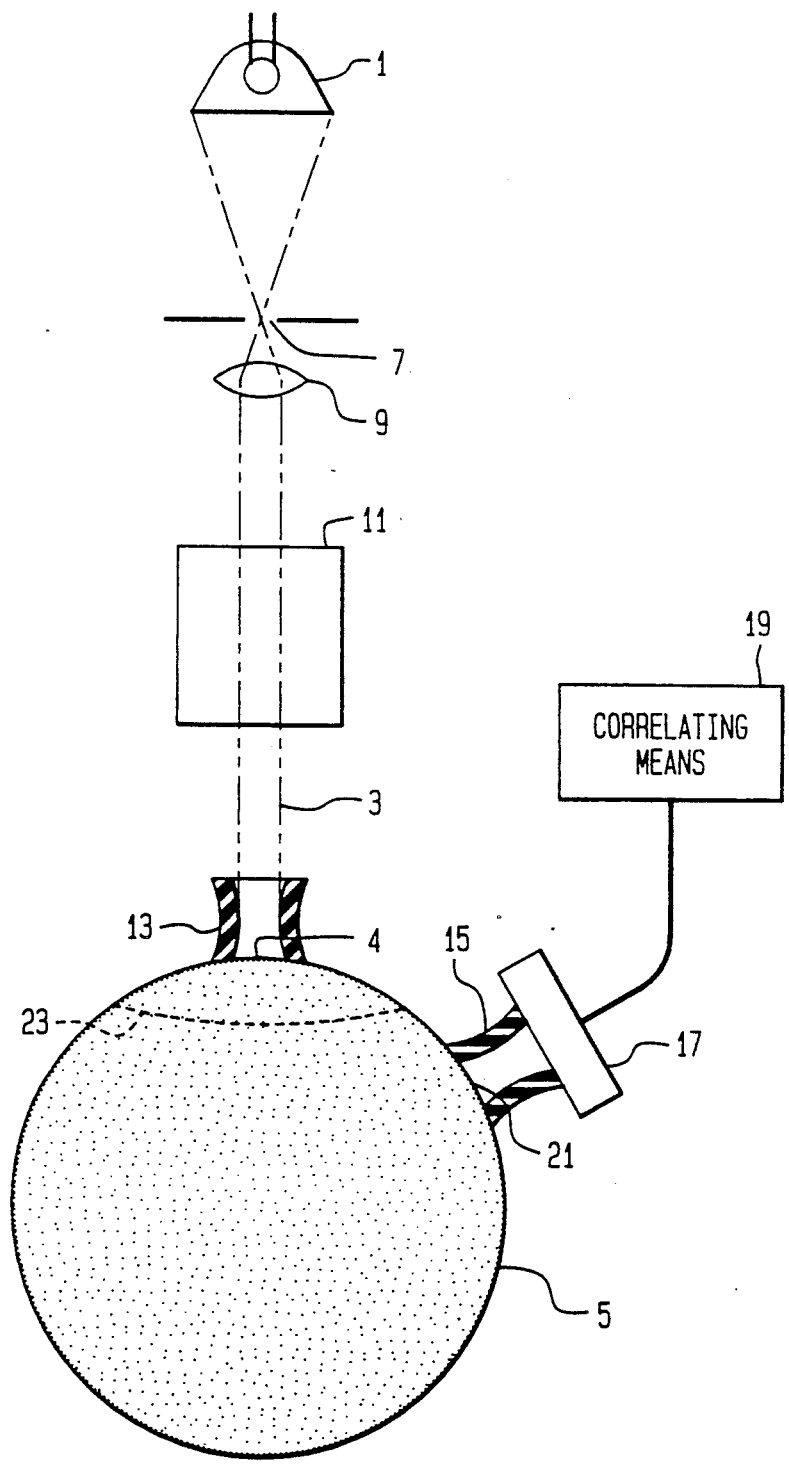
FIG. 1 is a schematic illustration of a device of the present invention, employing: a NIR source means which does not provide NIR in a plurality of wavelength bands, and; a wavelength band selection means positioned between the NIR source means and the fruit to be tested.
Figure 2:
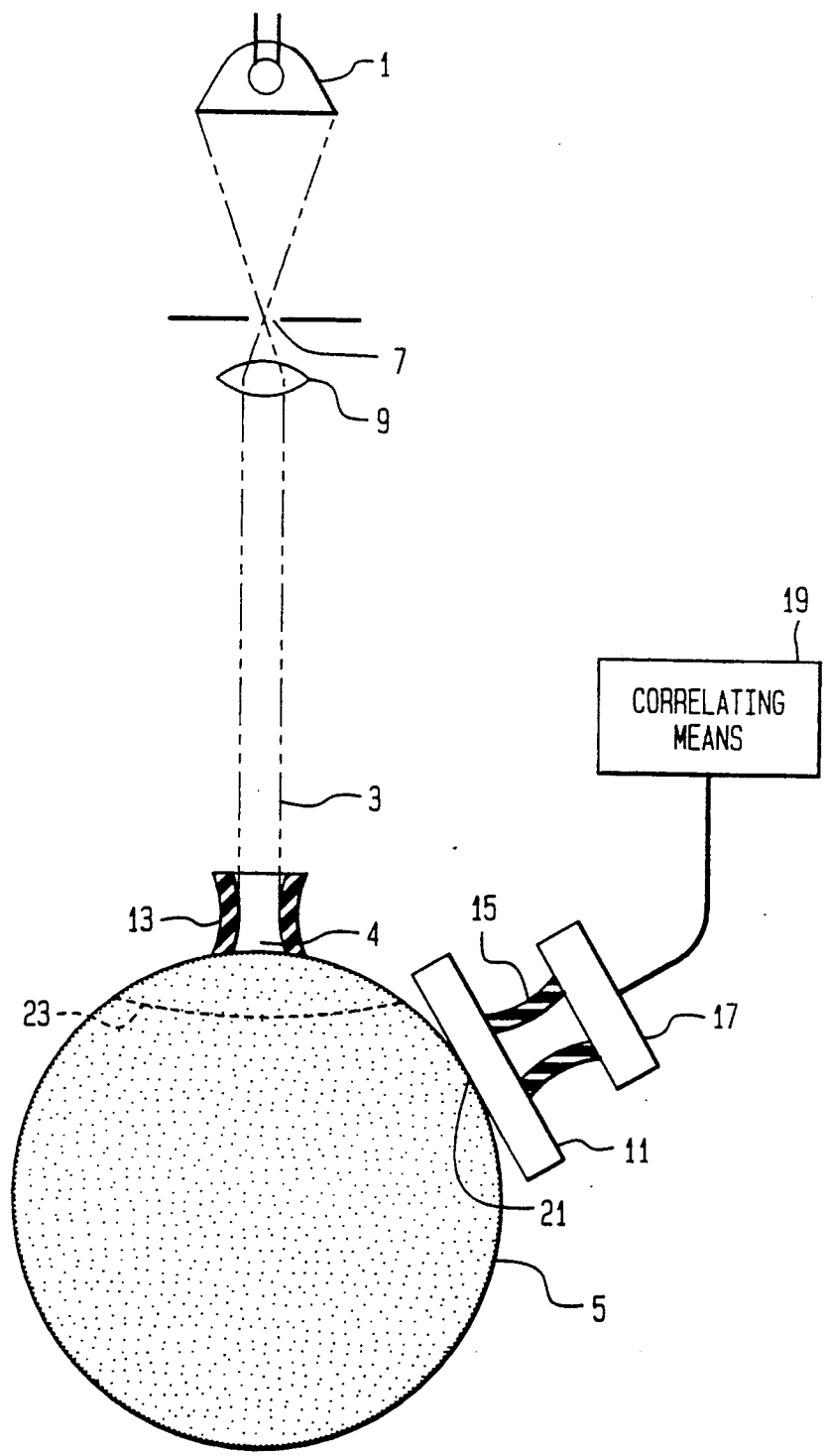
FIG. 2 is a schematic illustration of a device of the present invention, employing: a NIR source means which does not provide NIR in a plurality of wavelength bands, and; a wavelength band selection means positioned between the fruit to be tested and the intensity measurement means.
Figure 3:
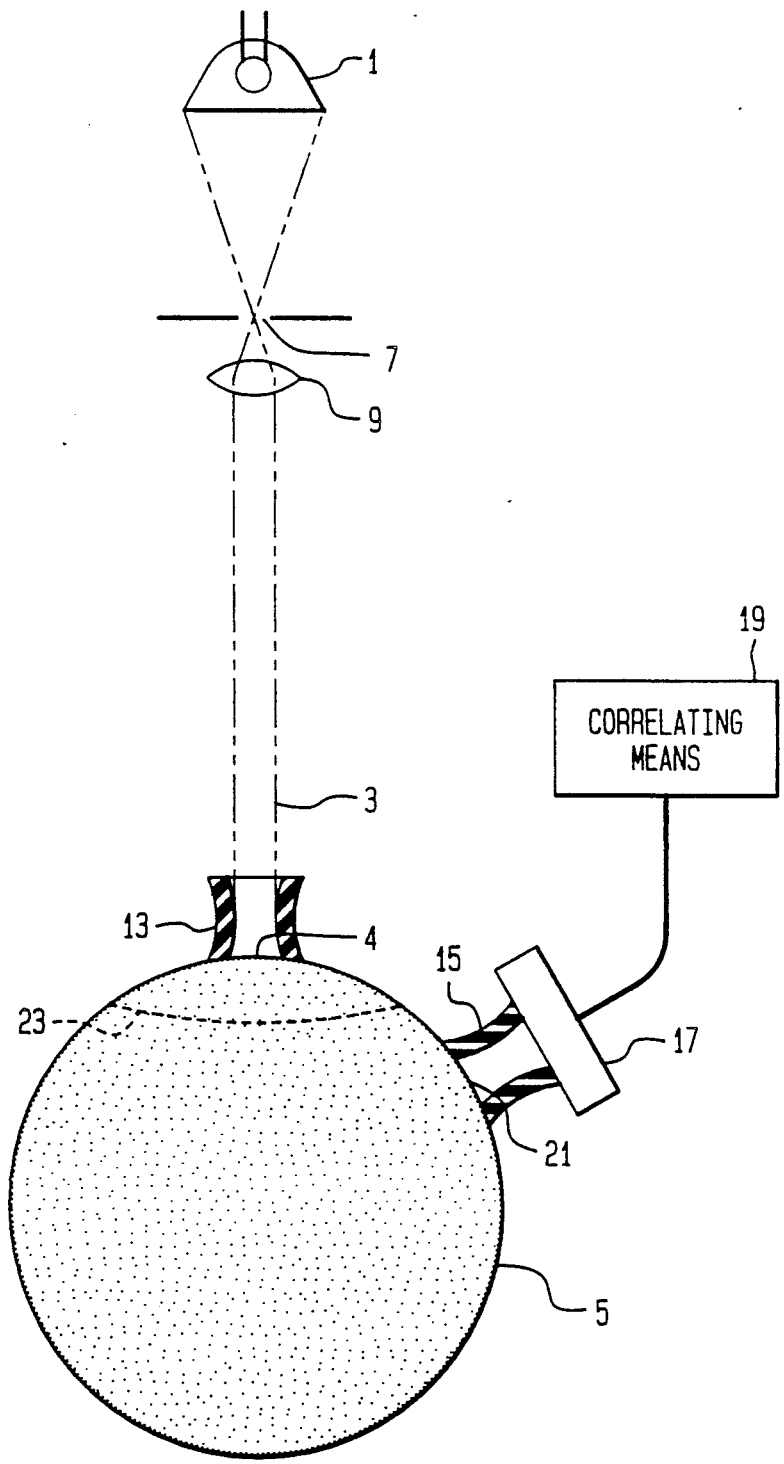
FIG. 3 is a schematic illustration of a device of the present invention employing a NIR source means which does provide NIR in a plurality of wavelength bands.

FIGS. 1-3 illustrate the basic components of three alternative embodiments, of devices for measuring in a nondestructive manner soluble solids in a fruit having a rind or skin in accordance with the present invention.

First, those elements which are common to all three embodiments will be described. Numeral 1 designates a near infrared radiation source means from which emanates near infrared radiation (NIR). Optionally, the NIR passes through an apertured plate designated 7 in order to permit beam collimation. Also, an optional collimating lens 9 may be provided. Optionally, the beam may then be passed through a flexible cylinder 13 which sits tightly against the rind or skin of fruit 5. The flexible cylinder 13 may be made of material which excludes radiation to which the intensity measurement means 17 is sensitive, thus providing means for excluding extraneous radiation. The NIR beam defines at the center thereof a beam center, and may typically be about 2 centimeters in diameter. A point (i.e. a first point) on the rind or skin of the fruit 5 where the center of NIR beam 3 intersects the rind or skin is designated in the drawings by numeral 4. The first point 4 may e.g. be about midway between the stem and blossom ends of the fruit. The NIR beam penetrates fruit 5, is scattered by the internal structure of the fruit and exits the fruit as exiting radiation through a plurality of points on the rind or skin of the fruit. The intensity of the exiting radiation is measured in each of a plurality of wavelength bands by intensity measurement means 17 which may be coupled to fruit 5 by a flexible cylinder 15. Exemplary intensity measurement means which may be employed in the present invention include those sensitive to radiation of wavelengths in the range of from about 800 nanometers to about 1050 nanometers, e.g. a silicon detector model HUV-4000B, EG&G Electro-Optics. Preferably, the cylinders 13 and 15 may be made of flexible material, such as rubber, so that the fruit 5 may easily be positioned in contact with both cylinders simultaneously. The intensity measurement means 17 defines a field of detection having a center. The point (i.e. a second point) on the rind or skin of the fruit where the center of said field of detection intersects the rind or skin is designed by the numeral 21 in FIGS. 1-3. The second point 21 may e.g. be about midway between the stem and blossom ends of fruit i.e. points 4 and 21 may be located on a cross section of the fruit which is about midway between the stem and blossom ends of the fruit. The intensity measurement means 17 is connected to correlating means 19 for correlating the measurements of intensities of said exiting radiation in each of a plurality of wavelength bands to a concentration of soluble solids in the fruit. Such correlating may take the form of one or more of the following methods; derivatizing the data with respect to wavelength, principle component analysis, partial least squares analysis, standard normal variable analysis, fourier transform analysis, simple regression, Norris regression, and multiple regression.

In order to produce soluble solids information the device and process must be used first in an instrument calibration procedure. Secondly, in a prediction procedure. The calibration for each type of fruit will yield a unique algorithm for the prediction of soluble solids. Once a calibration procedure has produced the prediction algorithm any number of predictions of soluble solids may be made by treating the wavelength data in precisely the same fashion as was done in the calibration procedure.

As an example of the calibration procedure intensity data at discrete wavelengths may be used to form four second derivatives with respect to wavelength. Use of the second derivative decreases experimental error arising from radiation scattering and variations in sample size. The four second derivatives may then be used as the variables in a four term multiple regression equation, e.g.

$$Y = a_0 + a_1x_1 + a_2x_2 + a_3x_3 + a_4x_4 \quad (EQN.\ 1)$$

where $a_0$ to $a_4$ are constants, $x_1$ to $x_4$ are second derivatives calculated from wavelength intensity data, and Y is soluble solids.

In the calibration procedure, a minimum of 36 fruits were measured by the above device and process. The soluble solids determined from a sample of inner tissue located between first point 4 and second point 21 is determined by a standard laboratory procedure. Constants $a_0$ to $a_4$ are determined by a multiple linear regression procedure which chooses the wavelengths and the parameters for second derivative calculation so as to maximize the correlation coefficient for the regression. For data acquired by a computerized data acquisition system, commercial software is available for performing this regression.

Once the constants $a_0$ to $a_4$ and the procedure for calculating second derivatives are determined, prediction of soluble solids in other samples of the same fruit cultivar may be done as follows: collect the same data as was done in the calibration phase; calculate the second derivatives in identical fashion as in the calibration phase, and; calculate Y (i.e. soluble solids) using equation 1.

This exemplary procedure now permits the estimation of soluble solids nondestructively in any member of the same fruit cultivar.

The differences in the various embodiments shown in FIGS. 1-3 will now be explained.

The embodiments of FIGS. 1 and 2 relate to those types of NIR source means which do not provide NIR in a plurality of wavelength bands. Typical of such NIR source means are incandescent source means such as a GE bulb 1392, 6 volts, driven at about 8.3 volts using a Kepko power supply (JQE 36 - 8(T)) in constant current mode. Other high intensity sources, free of spectral lines and generating substantial radiation of a wavelength within the range of from about 800 nanometers to about 1050 nanometers are also within the scope of this invention. The 800-950 nm region of the spectrum is important because this region contains information about both water and carbohydrates, is sufficiently weakly absorbing so as to permit radiation to pass through a fruit, yet avoids the effect of pigments characteristic of shorter, visible wavelengths. Thus, as shown in FIG. 1 a wavelength band selection means 11 may be positioned between NIR source means 1 and the fruit 5. In this position the wavelength band selection means 11 functions to select from the NIR emanating from the NIR source means 1 a plurality of wavelength bands. Alternatively, as illustrated in FIG. 2 the wavelength band selection means 11 may be positioned between the fruit 5 and the intensity measurement means. In this configuration the wavelength band selection means functions to select from the exiting radiation a plurality of wavelength bands. The aforementioned wavelength bands selection means may, for example, take the form of gratings, prisms, acousto-optic filters, a series of filters, devices employing fourier transform techniques and tilting assemblies such as that commercially available from NIR Systems, Silver Spring, Maryland.

In contrast to FIGS. 1 and 2, FIG. 3 relates to NIR source means 1 which provide NIR in a plurality of wavelength bands. Typical of such source means 1 are: tunable scanning lasers, laser diodes and infrared emitting diodes.

It is preferred that the aforementioned plurality of wavelength bands each have a band width of less than about 9 nanometers, e.g. from about 7 to about 9 nanometers. The use of multiple scans improves the signal to noise ratio and therefore use of many scans is desirable. Either mechanical or electronic scanning may be utilized.

It has surprising and unexpectedly been discovered that in order to successfully measure the soluble solids in fruits having a rind or skin, that the distance (measured along the rind or skin) between: (1) the point on the rind or skin where the center of the NIR beam intersects the rind or skin (i.e. point 4 in drawing FIGS. 1-3), and; (2) the point on the rind or skin where the center of the field of detection intersects the rind or skin (i.e. point 21 in drawing FIGS. 1-3); must be at least about 8 centimeters. The locus of points designated 23 illustrates a distance of about 8 centimeters from point 4. Thus, the present invention encompasses positioning the NIR source means 1 and intensity measurement mean 17 relative to each other, so that the point on the rind or skin where the center of the field of detection intersects the rind or skin is on or outside of the locus of points 23. This configuration of the NIR source means and the intensity measurement means helps to insure that some of the NIR which reaches the intensity measurement means has penetrated through and has been scattered from internal fruit tissue.

Data acquisition may include an initial scan when a standard scattering material (e.g. a TEFLON TM block) has been placed in measurement position. Then, a fruit is put in measurement position and scanned. The log of the ratio of the standard material scan to that of the fruit gives an optical-density-like data set which then can be treated mathematically and regressed statistically on soluble solids data.

Examples of fruit which may be tested in accordance with the present invention include melons, drupes and pome fruit. Although it should be clearly understood that the instant invention may be practiced with any of a wide variety of fruits having a skin or rind.

EXAMPLE

The following example is intended only to further illustrate the invention and is not intended to limit the scope of the invention as defined by the claims:

A set of 36 Honeydew melons was scanned in accordance with the present invention and soluble solids analysis by a standard refractometer method was done on the inner tissue in the region of the melon between the incident beam and the detector position. Melon soluble solids data are then regressed on a parameter calculated from the spectral data. Possible parameter can be the first or second derivative of the spectral data or a ratio of second derivatives (Norris regression). The use of commercially available software permits the calculation of all possible regressions (one for each wavelength) and selects the one having the largest correlation coefficient in magnitude. Multiple regression is accomplished by adding one term at a time (each associated with a different wavelength) and maximizing the total correlation coefficient. Repeated application of the above steps lead to an optimized regression with respect to the parameters of the derivative calculation.

Verification of the regression equation done by the use of another set of melons in which each melon is measured spectroscopically and its soluble solid concentration determined by the standard refractometer analysis as was done for the calibration melon set. The standard error of prediction (SEP) using the verification melon set should be of the same order as the standard error of calibration (SEC) determined from the calibration melon set.

Here, SEC is defined as follows:

$$SEC = \left( \frac{1}{(n - P - 1)} \sum_{i=1}^{n} ei^2 \right)^{\frac{1}{2}}$$

where:

ei is the difference between the NIR soluble solids and the laboratory solids value, P is the number of wavelengths in the regression equation and, n is the number of data points taken.

SEP is defined as follows:

$$SEP = \left( \frac{1}{(n - 1)} \sum_{i=1}^{n} (ei - \overline{e})^2 \right)^{\frac{1}{2}}$$

where:

$$\text{the base } \overline{e} = \frac{1}{n} \sum_{i=1}^{n} ei$$

Figure 4:
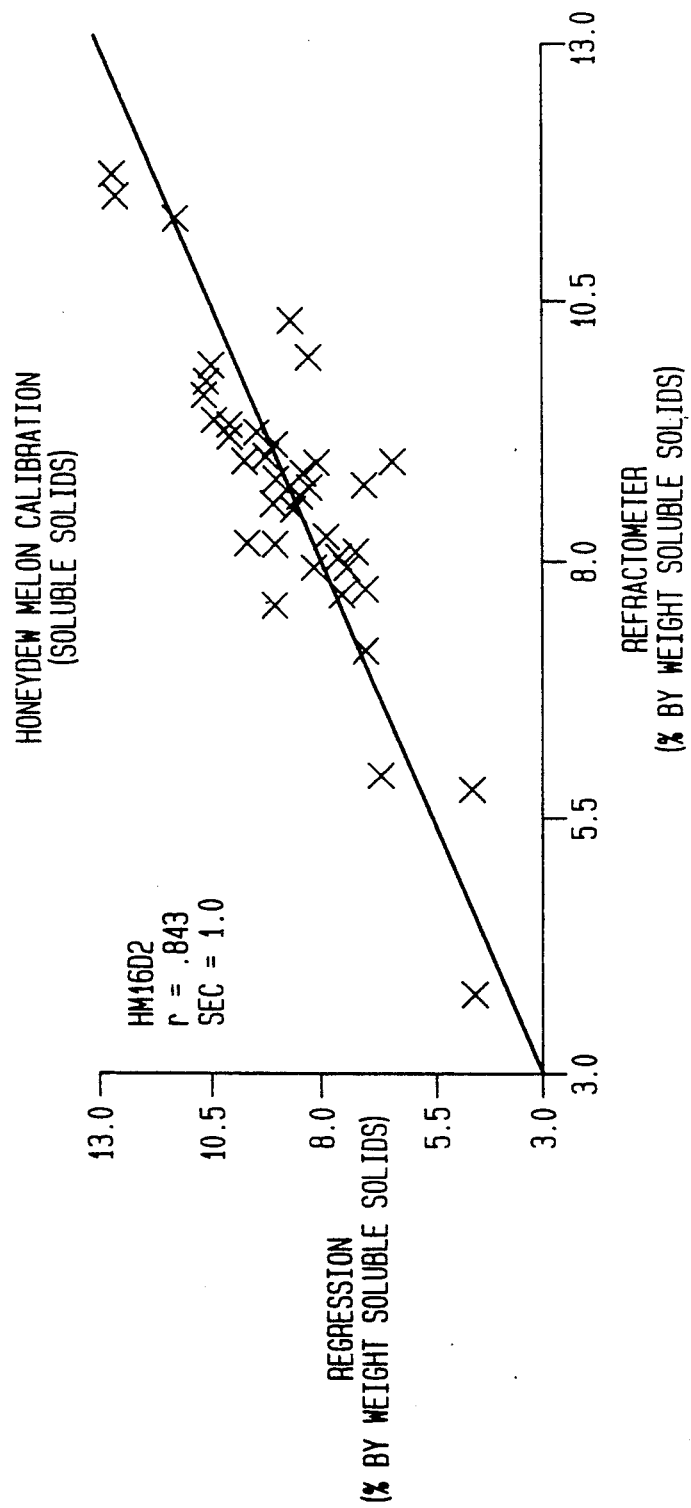
FIG. 4 is a graph of regression % by weight soluble solids vs. refractometer % by weight soluble solids, for Honeydew melons, showing results obtained by use of the present invention.

The results are shown in FIG. 4. As can be seen in FIG. 4, predicted soluble solids versus the refractometer determination for a calibration set of 34 Honeydew melons shows that the standard error of calibration (SEC) is 1.0.

The foregoing detailed descriptions and examples are given merely for purposes of illustration. Modifications and variations may be made therein without departing from the spirit and scope of the invention.

INDEX OF ELEMENTS DESIGNATED BY A NUMERAL

1 NIR source means
3 NIR beam
4 A first point
5 Fruit having a rind or skin
7 Optional apertured plate
9 Optional Collimating lens
11 Wavelength band selection means
13 Flexible cylinder
15 Flexible Cylinder
17 Intensity measurement means
19 Correlating means
21 A second point
23 Locus of points about 8 centimeters from first point 4

We claim:

1. A device for measuring in a nondestructive manner soluble solids in a fruit having a rind or skin, comprising:

(a) a near infrared radiation source means for providing a beam of near infrared radiation of sufficient intensity to penetrate said fruit and be scattered by the internal structure of said fruit and exit said fruit as exiting radiation through a plurality of points on said rind or skin of said fruit;

(b) wavelength band selection means for selecting from either; (1) said near infrared radiation from said near infrared radiation source means or, (2) said exiting radiation; a plurality of wavelength bands;

(c) intensity measurement means, operably associated with said wavelength band selection means, for measuring the intensity of said exiting radiation in each of said plurality of wavelength bands, said intensity measurement means having a field of detection and a center of said field of detection;

(d) correlating means, operably associated with said intensity measurement means, for correlating the measurements of intensities of said exiting radiation in each of said plurality of wavelength bands to a concentration of soluble solids in said fruit; and (e) wherein said near infrared radiation source means and said intensity measurement means are positioned such that when a said fruit is positioned within the device, the distance measured along said rind or skin of said fruit between: (1) a first point on said rind or skin where the center of said beam intersects said rind or skin, and: (2) a second point on said rind or skin where said center of said field of detection intersects said rind or skin; is at least about 8 centimeters.

2. The device of claim 1 wherein said near infrared radiation source means is an incandescent source.

3. The device of claim 1 wherein said wavelength band selection means is selected from the group consisting of gratings, prisms, acousto-optic filters, a series of filters and devices employing fourier transform techniques.

4. A device for measuring in a nondestructive manner soluble solids in a fruit having a rind or skin, comprising:

(a) a near infrared radiation source means for providing a beam of near infrared radiation in a plurality of wavelength bands of sufficient intensity to penetrate said fruit and be scattered by the internal structure of said fruit and exit said fruit as exiting radiation through a plurality of points on said rind or skin of said fruit;

(b) intensity measurement means for measuring the intensity of said exiting radiation in each of said plurality of wavelength bands, said intensity measurement means having a field of detection and a center of said field of detection;

(c) correlating means, operably associated with said intensity measurements means, for correlating the measurements of intensities of said exiting radiation in each of said plurality of wavelength bands to a concentration of soluble solids in said fruit; and (d) wherein said near infrared radiation source means and said intensity measurement means are positioned such that when a said fruit is positioned within the device, the distance measured along said rind or skin of said fruit between: (1) a first point on said rind or skin where the center of said beam intersects said rind or skin, and: (2) a second point on said rind or skin where said center of said field of detection intersects said rind or skin; is at least about 8 centimeters.

5. The device of claim 4 wherein said near infrared radiation source means is selected from the group consisting of tunable scanning lasers, laser diodes and infrared emitting diodes.

6. The device of either claim 1 or 4, wherein said near infrared radiation source means produces radiation of a wavelength within the range of from about 800 nanometers to about 1050 nanometers.

7. The device of either claim 1 or 4, wherein said plurality of wavelength bands each have a band width of less than about 9 nanometers.

8. The device of claim 7 wherein said plurality of wavelength bands each have a band width of about 7 to about 9 nanometers.

9. The device of either claim 1 or 4 further including means for excluding extraneous radiation from said intensity measurement means.

10. The device of claim 9 wherein said means for excluding extraneous radiation includes a flexible cylinder of material which excludes radiation to which said intensity measurement means is sensitive.

11. The device of either claim 1 or 4 wherein said intensity measurement means includes a silicon detector cell.

12. A process for measuring in a nondestructive manner soluble solids in a fruit having a rind or skin, comprising:
(a) directing a beam of near infrared radiation from a near infrared radiation source means into a said fruit so that said near infrared radiation penetrates said fruit and is scattered by the internal structure of said fruit and exits said fruit as exiting radiation through a plurality of points on said rind or skin of said fruit;
(b) selecting from either; (1) said near infrared radiation from said near infrared radiation source means or, (2) said exiting radiation; a plurality of wavelength bands;
(c) measuring the intensity of said exiting radiation in each of said plurality of wavelength bands using intensity measurement means having a field of detection and a center of said field of detection;
(d) correlating the measurements of intensities of exiting radiation in each of said plurality of wavelength bands to a concentration of soluble solids in said fruit; and
(e) wherein said near infrared radiation source means and said intensity measurement means are positioned such that the distance measured along said rind or skin of said fruit between: (1) a first point on said rind or skin where the center of said beam intersects said rind or skin, and: (2) a second point on said rind or skin where said center of said field of detection intersects said rind or skin; is at least about 8 centimeters.

13. The process of claim 12 wherein said near infrared radiation source means is an incandescent source.

14. The process of claim 12 wherein said wavelength band selection means is selected from the group consisting of gratings, prisms, acousto-optic filters a series of filters and devices employing fourier transform techniques.

15. A process for measuring in a nondestructive manner soluble solids in a fruit having a rind or skin, comprising:
(a) directing a beam of near infrared radiation in a plurality of wavelength bands from a near infrared radiation source means into a said fruit so that said near infrared radiation penetrates said fruit and is scattered by the internal structure of said fruit and exits said fruit as exiting radiation through a plurality of points on said rind or skin of said fruit;
(b) measuring the intensity of said exiting radiation in each of said plurality of wavelength bands using intensity measurement means having a field of detection and a center of said field of detection;
(c) correlating the measurements of intensities of exiting radiation in each of said plurality of wavelength bands to a concentration of soluble solids in said fruit; and
(d) wherein said near infrared radiation source means and said intensity measurement means are positioned such that the distance measured along said rind or skin of said fruit between: (1) a first point on said rind or skin where the center of said beam intersects said rind or skin, and: (2) a second point on said rind or skin where said center of said field of detection intersects said rind or skin; is at least about 8 centimeters.

16. The process of claim 15 wherein said near infrared radiation source means is selected from the group consisting of tunable scanning lasers, laser diodes and infrared emitting diodes.

17. The process of either claim 12 or 15, wherein said near infrared radiation source means produces radiation of a wavelength within the range of from about 800 nanometers to about 1050 nanometers.

18. The process of either claim 12 or 15, wherein said plurality of wavelength bands each have a band width of less than about 9 nanometers.

19. The process of claim 18 wherein said plurality of wavelength bands each have a band width of about 7 to about 9 nanometers.

20. The process of either claim 12 or 15 further including means for excluding extraneous radiation from said intensity measurement means.

21. The process of claim 20 wherein said means for excluding extraneous radiation includes a flexible cylinder of material which excludes radiation to which said intensity measurement means is sensitive.

22. The process of either claim 12 or 15 wherein said intensity measurement means includes a silicon detector cell.

23. The process of either claim 12 or 15 wherein said fruit is selected from the group consisting of melons, drupes and pome fruit.

* * * * *